(12) United States Patent
Tulleken et al.

(10) Patent No.: US 8,777,971 B2
(45) Date of Patent: Jul. 15, 2014

(54) DEVICE AND METHOD FOR JOINING VESSELS IN ANASTOMOSIS

(75) Inventors: Cornelis Antonius Franciscus Tulleken, Utrecht (NL); Rik Hendricus Jacobus Mansvelt Beck, Doorn (NL); Tristan Theodoris Petrus Cornelis van Doormaal, Utrecht (NL)

(73) Assignee: AMJ bv (NL)

( * ) Notice: Subject to any disclaimer, the term of this patent is extended or adjusted under 35 U.S.C. 154(b) by 1517 days.

(21) Appl. No.: 11/868,446

(22) Filed: Oct. 5, 2007

(65) Prior Publication Data

US 2008/0109019 A1    May 8, 2008

Related U.S. Application Data

(60) Provisional application No. 60/914,800, filed on Apr. 30, 2007, provisional application No. 60/829,731, filed on Oct. 17, 2006.

(51) Int. Cl.
*A61B 17/08* (2006.01)
*A61B 17/11* (2006.01)

(52) U.S. Cl.
CPC ......... *A61B 17/11* (2013.01); *A61B 2017/1107* (2013.01); *A61B 2017/1135* (2013.01)
USPC ........................................ 606/155

(58) Field of Classification Search
USPC ......................... 606/151–153, 213
See application file for complete search history.

(56) References Cited

U.S. PATENT DOCUMENTS

| 3,805,793 | A | | 4/1974 | Wright |
| 4,523,592 | A | * | 6/1985 | Daniel .......................... 606/153 |
| 4,917,087 | A | * | 4/1990 | Walsh et al. .................. 606/153 |
| 5,259,835 | A | | 11/1993 | Clark et al. |
| 5,797,920 | A | | 8/1998 | Kim |
| 5,797,933 | A | | 8/1998 | Snow et al. |
| 5,868,763 | A | * | 2/1999 | Spence et al. ................. 606/153 |
| 5,964,750 | A | * | 10/1999 | Tulleken et al. ................ 606/15 |
| 6,165,185 | A | * | 12/2000 | Shennib et al. ............... 606/155 |
| 6,193,734 | B1 | | 2/2001 | Bolduc et al. |
| 6,433,096 | B1 | | 8/2002 | Hickey |
| 6,869,437 | B1 | * | 3/2005 | Hausen et al. ................ 606/153 |
| 6,942,675 | B1 | * | 9/2005 | Vargas .......................... 606/153 |
| 7,371,243 | B1 | * | 5/2008 | Nielsen et al. ................ 606/142 |

(Continued)

FOREIGN PATENT DOCUMENTS

| BE | WO 2004/096059 A1 * | 11/2004 |
| EP | 2083712 A1 | 8/2009 |

(Continued)

OTHER PUBLICATIONS

"European Application Serial No. 07818996.6, Office Action mailed Jun. 18, 2009", 2 pgs.

(Continued)

*Primary Examiner* — Tuan V Nguyen

(74) *Attorney, Agent, or Firm* — Schwegman, Lundberg & Woessner, P.A.

(57) ABSTRACT

Devices and methods for attaching an end of a body vessel to another body vessel are disclosed. An adhesive may be used along with a rigid member having one or more protrusions. The invention is useful in surgery, especially vascular surgery and the creation of anastomoses.

18 Claims, 11 Drawing Sheets

(56) References Cited

U.S. PATENT DOCUMENTS

| | | |
|---|---|---|
| 7,371,543 B2 * | 5/2008 | Pedersen et al. .............. 435/69.1 |
| 2004/0210302 A1 * | 10/2004 | Scholz et al. ................. 623/1.31 |
| 2006/0025790 A1 | 2/2006 | De Winter et al. |
| 2006/0030869 A1 | 2/2006 | Loshakove |
| 2006/0116699 A1 | 6/2006 | Bombard |

FOREIGN PATENT DOCUMENTS

| | | |
|---|---|---|
| WO | 03020106 A | 3/2003 |
| WO | WO-03020106 A2 | 3/2003 |
| WO | 2004096059 A | 11/2004 |
| WO | WO-2004096059 A1 | 11/2004 |
| WO | 2005/060836 A2 | 7/2005 |

OTHER PUBLICATIONS

"European Application Serial No. 07818996.6, Response filed Jul. 9, 2009 to Office Action mailed Jun. 18, 2009", 3 pgs.

"International Application Serial No. PCT/EP2007/008925, International Preliminary Report on Patentability mailed Apr. 22, 2009", 8 pgs.

"International Application Serial No. PCT/EP2007/008925, International Search Report mailed Mar. 13, 2008", 4 pgs.

* cited by examiner

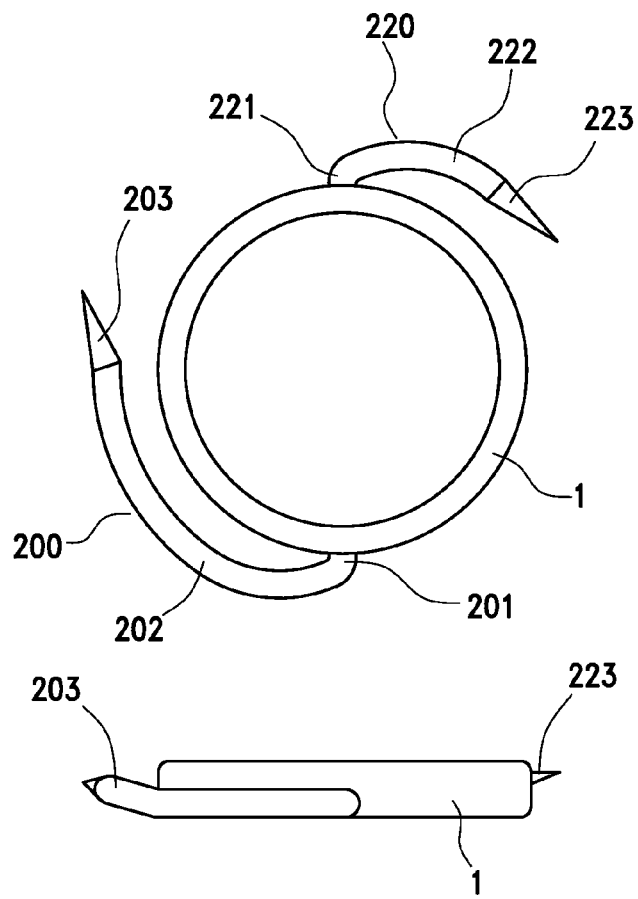
FIG. 15A
FIG. 15B
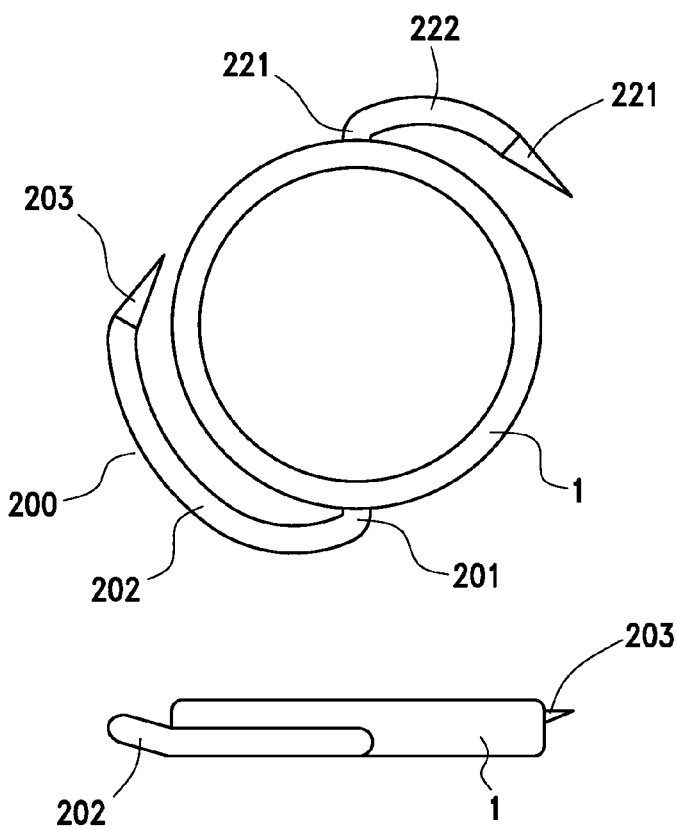
FIG. 16A
FIG. 16B

DEVICE AND METHOD FOR JOINING VESSELS IN ANASTOMOSIS

This application claims the benefit of U.S. Provisional Application No. 60/914,800, filed Apr. 30, 2007 and U.S. Provisional Application No. 60/829,731, filed Oct. 17, 2006, which are hereby incorporated herein by reference in their entireties.

FIELD OF THE INVENTION

The invention relates to the field of surgery, in particular neurosurgery, including methods for fusing or otherwise connecting body tissues, such as blood vessels. In particular, the invention is useful during vascular surgery for creating anastomoses and for vascular reconstruction.

BACKGROUND OF THE INVENTION

Fusion of body tissues for repairing tissues, including when closing surgical openings, as well as for creating new connections of tissue, such as an anastomosis for vascular bypass, has been an important concern of surgeons since surgical procedures were first used.

In vascular surgery, anastomoses need to be made to join vessels with other vessels or open volumes through which blood can flow. Such tissue connections should be made blood-tight, and be able to withstand the pressures and forces acting on them in vivo.

The creation of a fluid or blood-tight (hemostatic) and mechanically stable connection such as for an anastomosis takes considerable time, skill, and care and is prone to complications. Even slight misalignment, asymmetric tension, introduction of foreign material, or wrong tissue types may trigger bodily responses, such as thrombogenesis, coagulation, or scar formation, which may have a detrimental effect on the patency (i.e., the ability to let fluids pass) of a connection, or cause immediate or delayed leakage of vessels or vessel damage, later followed by dehiscence, pseudo aneurysm, or anastomotic aneurysm formation.

In most cases, tissue joints such as the ones required in an anastomosis are created when the surgeon sutures or staples tissues, such as vessel wall tissues, together. Tissue soldering, tissue welding, and the use of adhesives have also been discussed, but the first two methods are not widely used, while adhesives are generally only used in combination with sutures, clips, or mechanical closures.

A common concern associated with the use of adhesives, especially when connecting blood vessels, is that the adhesive may enter the bloodstream leading to blockage and other complications. In addition, using adhesives alone to join body tissues can result in mechanically unsafe connections or connections with insufficient patency. The tissues to be joined can be under a different tension during surgery than in vivo, or can be subject to varying tensions, which can result in the weakening or breaking of an adhesive bond between the tissues or a change in the form of a connection. Although methods of using adhesives to connect a graft to an unoccluded recipient vessel were described decades ago (see, U.S. Pat. No. 3,805,793 to Wright, which was issued in 1974), adhesives are generally not used by themselves in surgical procedures for the reasons stated above, despite the apparent advantages that adhesives seem to offer, in particular, ease of application.

In many clinical applications, it is advantageous to perform anastomosis without occluding the recipient vessel. This becomes particularly important when the recipient vessel involved performs a vital function. In generally sensitive or critical organs such as the brain, occluding a recipient vessel even temporarily is often disadvantageous. A technique commonly referred to as the ELANA (Excimer Laser Assisted Nonocclusive Anastomosis) technique, is used in clinical practice to create an anastomosis without occluding the recipient vessel (see also, U.S. Pat. No. 5,964,750 (Tulleken et al.)). This technique is, e.g., used by neurosurgeons in bypass surgery. After attaching an implantable ring around a distal portion of the graft vessel, the end of the graft vessel is folded back over the ring creating an orifice that is reinforced by this ring. This reinforced orifice of the graft vessel is attached to the wall of the recipient vessel of the patient. This attachment is generally performed by suturing the graft vessel to the recipient vessel via eight sutures approximately. Depending on the skill of the surgeon and the conditions found in the patient, the attachment will take generally anywhere from half an hour to one hour or more. A laser catheter is then inserted into the graft vessel to create an opening between the graft and recipient vessel. During the entire procedure, blood will continue to flow within the recipient vessel, avoiding the temporary shut off of the bloodstream associated with many other anastomosis methods.

There exists a need in the art for an improved method for attaching body vessels to each other, as well as for an improved anastomotic surgery aid for forming connections between body vessels. Therefore, the purpose of this invention is to fulfill this andor other needs in the art which will become apparent to the skilled artisan once given the following disclosure.

SUMMARY OF THE INVENTION

In general, the present invention addresses the above-described needs by providing an improved method for attaching body vessels to each other as well as for an improved anastomotic surgery aid.

In one aspect, the invention provides a way to join tissues, in particular body vessels andor grafts, which is easier and quicker than conventional methods. The invention can be used in certain embodiments to produce an anastomosis, which can be easily and quickly made (so that time for surgery and anaesthesia are kept to a minimum), and leaves few possibilities for complications and preferably has a good short-, mid- and long-term patency rate, as well as causing no or little leakage of blood.

In another aspect, the invention provides methods, devices, and kits to attach the end of a donor vessel, e.g., a bypass graft, onto the side of a recipient vessel, such as an artery, by using a rigid member and an adhesive, optionally in combination with, e.g., sutures or staples. Kits also may include an applicatordevice for connecting body vessels as well as a tissue adhesive along with the rigid member, and preferably also a tool such as a microscissor or scalpel for making incisions in the graft wall.

In one embodiment, the rigid member may be a ring or loop structure, which may be circular or oval-shaped and be substantially flat, in order to receive one of the vessels, generally the donor vessel. The rigid member may also have at least one, and preferably two, in certain embodiments three or four, protrusions, such as spikes, pins, needles, or other pointed, preferably elongated, structures. The protrusions do not need to be straight, and may also be bent to different degrees andor in various directions relative to the rigid member. These protrusions facilitate or enable the attachment of the donor to the recipient vessel andor vice versa, but may also facilitate or enable the attachment of a rigid member to the vessel, which it preferably encircles.

In another aspect, a donor vessel, attached to the rigid member can be further attached to a recipient vessel, such as an artery, with one or more simple, and often minimal intrusive movements, thereby using the anastomostic surgery aid of the present invention.

The invention is in one embodiment directed to a method for attaching vessels for anastomosis comprising:
(a) providing a donor vessel having a wall comprising an inner and an outer surface and an open end,
(b) providing a wall of a recipient vessel,
(c) attaching a rigid member at said inner andor outer surface of the donor vessel at a position proximate of said open end,
(d) providing at least one incision from said open end towards said position of said rigid member terminating at or before said position to form a tail structure and an orifice reinforced by said rigid;
(e) establishing a contact between said donor and said recipient vessel via said orifice;
(f) forming a contact plane between the inner surface of said donor vessel at said tail structure and said wall of said recipient vessel form; and
(g) attaching the donor vessel to the recipient vessel via said contact plane andor rigid member.

The attaching in (g) may comprise applying an adhesive to at least parts of said contact plane or may essentially consist of applying an adhesive to at least parts of said contact plane. The recipient vessel may be a blood vessel and the blood flow through said blood vessel may optionally be unoccluded at least during (a) to (f). The distance between said position of the rigid member and said orifice may be about ½ to three times the diameter of said donor vessel. The incision may terminate at a distance of between about ½ and about 2 times a thickness of the wall of said donor vessel.

The rigid member may be a ring structure, which is attached to the outer surface of said donor vessel and may comprise protruding pointed structures to optionally attach said donor to said recipient vessel. The recipient vessel may, upon engagement with said ring structure via said protruding pointed structures, be stretched between about 10% and about 20% at least between at least two of said protruding pointed structures.

The method may further comprise inserting a device, e.g. a laser catheter having some or all of the elements of the laser catheter shown in FIGS. 5A and 5B into said donor vessel, wherein said device removes a portion of the wall of the recipient vessel to connect an interior of the donor vessel to the interior of the recipient vessel.

The invention is also directed at an anastomostic surgery aid for connecting a donor to a recipient vessel comprising: a ring structure sized to extend around the donor vessel; and at least two protruding pointed structures extending from said ring structure to attach the donor vessel to the recipient vessel.

At least a portion of a first andor a second of said protruding pointed structures may be substantially in a plane defined by the ring structure. At least a portion of the first of said protruding pointed structures may extend substantially parallel to the outer circumference of the ring structure. A second of said protruding pointed structures may extend straight from said ring structure andor bends into a direction defined by said first protruding pointed structures. At least a portion of the second of said protruding pointed structures may also extend substantially parallel to the outer circumference of the ring structure. The distal portion of at least one of said protruding pointed structures extend at an angle out of the plane defined by the ring structure, e.g., at an angle between about 10° and about 30°. The protruding pointed structures may be attached symmetrically at said ring structure.

The invention is also directed at a surgery kit comprising: a device for connecting body vessels, the anastomostic surgery aid as described above, and instructions of using the anastomostic surgery aid with said device.

The invention is also directed at the use of laser catheter in combination with the attachment of tail structures of a donor vessel to a recipient vessel, involving optionally, adhesive andor a rigid structure, in particular a ring structure, preferably having protrusions as described herein.

BRIEF DESCRIPTION OF THE DRAWINGS

FIGS. 15A and 15B are a top and lateral view, respectively, of another preferred rigid member having two hooks of differing length as protruding pointed structures each of which extending substantially parallel to the circumference of the rigid member. The tips of both hooks point upwards out of a plane defined by the rigid member.

FIGS. 16A and 16B are a top and lateral view, respectively, of another preferred rigid member having two hooks of differing length as protruding pointed structures each of which extending substantially parallel to the circumference of the rigid member. The tips of both hooks are directed upwards out of a plane defined by the rigid member, the longer of the two hooks points towards the rigid member.

In FIG. 17A the protruding pointed structures are all hooks pointing into one general direction, while in 17B one of the hooks is replaced by a pin.

DETAILED DESCRIPTION OF VARIOUS AND PREFERRED EMBODIMENTS OF THE INVENTION

Anastomosis generally refers to the process of connecting body vessels such as intracranial vessels or vessels in the gastrointestinal tract, bladder, urinary tract, and ovarian tract, as well as blood vessels such as arteries, andor veins, shunts, or bypass grafts, whereby the grafts may be either autologous, donated, or artificially made.

Described herein are methods for attaching a donor vessel, which includes the body vessels described above, including rerouted body vessels such as rerouted arteries, but in particular grafts such as a bypass grafts, which may include, for example, autologous veins, artery transplants, or artificial vessel prostheses, onto the side of a recipient vessel, for example, the gastrointestinal tract of a patient or an artery, with the help of a rigid member, and optionally an adhesive, along with optionally other means for attachment, such as sutures or staples.

Figure 1A:
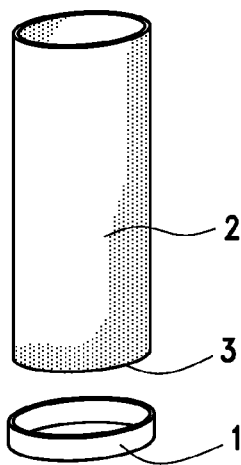
FIGS. 1A to 1D depict a rigid member and its attachment to a donor and recipient vessel.
Figure 1B:
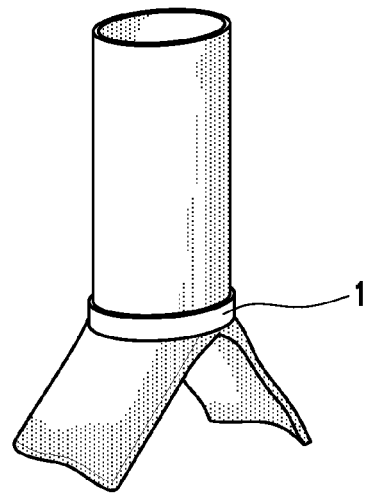

In certain embodiments, the rigid member forms a loop or ring, and may preferably have a circular or oval shape and may be substantially flat. A rigid member that forms a loop or ring is also referred to herein as a "ring structure." FIG. 1A shows a simple ring 1 and the end of a donor vessel 2 such as a graft. The donor vessel (in the following just referred to as a "graft") may be fed through the ring as shown in FIG. 1B and be attached at the donor vessel, preferably at a relatively small distance from an open end 3 of the graft, preferably so that, in the uses described herein, the normal of the ring is substantially perpendicular to the axis of the recipient vessel such as an artery. This configuration often corresponds to the ring being attached normal to the axis of the graft. In particular, the ring may be attached relative to the end of, e.g., the graft as depicted in FIG. 1A, at a distance of about ¼ to 4 times, preferably between about ½ and 3 times, even more preferably about ½ and 2 times the diameter of the graft. In embodiments in which the rigid member is a ring, the inner diameter of said ring will often have substantially the same diameter as a typical graft.

At least one incision can be made into the graft wall from its open end, in an axial direction towards the ring, ending at, or preferably just short of, the ring, preferably at a distance of between about ½ and about 2 times, including, for example, between about ½ and about 1 time or about 1½ times, and between about 1 time and about 1½ or about 2 times, the thickness of the graft wall. FIG. 1B shows the end of the graft after attachment of the ring and cutting of the graft. An applicator, in particular an internal applicator, that will be described in more detail below, may be used to stabilize the walls of very thin vessels during at least the steps shown in FIG. 1A and FIG. 1B. In the embodiment shown, two opposing incisions were made. However, any other, preferably even number of such incisions may be made, preferably substantially evenly spaced around the graft's circumference. In one preferred embodiment, four incisions are made. These incisions may be made by, e.g., microscissors or a scalpel, by perforating and tearing or, in certain embodiments, just tearing. Also as shown in FIG. 1B, the graft wall between the end of the graft and the ring can then be lifted like a coattail 4 (a structure which is also referred to herein as "tail structure").

Figure 1C:
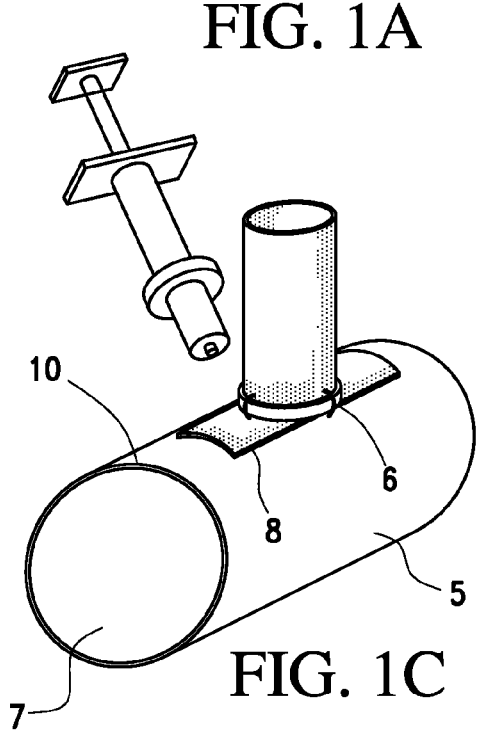
Figure 1D:
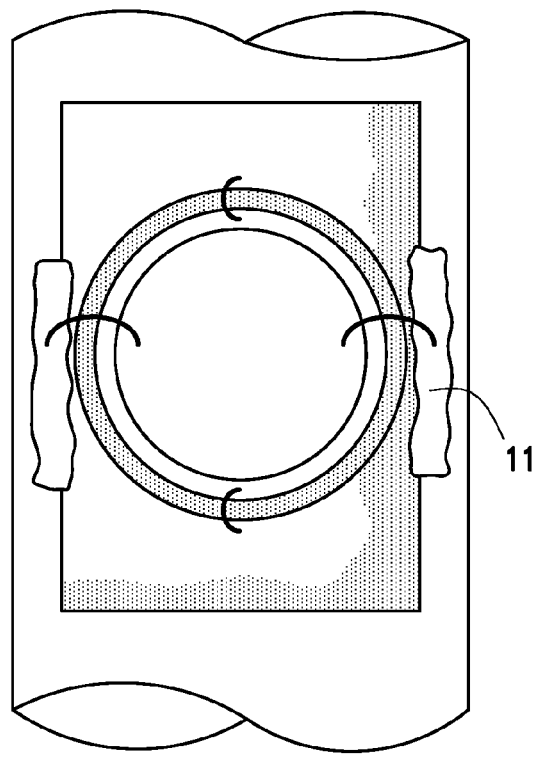

FIGS. 1B, 1C, and 1D disclose an anastomostic surgery aid having two tail structures that comprise substantially matching tail structures.

Generally after the ring has been attached, the graft can be set onto the outer wall of a recipient vessel 5 such as an artery at the desired position. The graft may be fixed therewith, e.g., sutures 6 (FIG. 1C), or clips, with the coattails extending away from the graft lumen 7 on the outside of the artery creating a contact plane 8 between the inner surface 9 of the graft at the coattails and the outer wall 10 of the recipient vessel 5. A contact plane refers herein to an extended surface area.

An applicator, which may be used as described above andor also to temporarily fix the graft to the artery, is preferably fed through the graft lumen to deliver vacuum suction at the applicator's tip in order to hold the graft onto the artery wall. Such an applicator will preferably have a protrusion at, or preferably a little distance from its tip (such as the one described on the ELANA catheter in U.S. Pat. No. 5,964,750, which is incorporated herein by reference) that pushes against the ring, and thereby pushes the graft wall below the ring firmly onto the artery wall. The vacuum suction that allows the application to, e.g., the recipient artery wall, avoids a net force on the recipient artery wall, assuring that the graft can be attached corresponding to natural conditions with regards to shape and tension of the concerned vessel walls.

Adhesive 11 can be applied under the coattails, as shown in FIGS. 1C and 1D by lifting the coattails 4 and applying the adhesive underneath them. A substantial portion of the contact plane 8 may be coated with adhesive. The coattails may then be lightly pressed onto the artery wall ensuring a firm fixation at least until healing processes take over. In a preferred embodiment, the adhesive 11, which may primarily act as a sealant, may also be applied proximal to the ring between the coattails as shown in FIG. 1D, thus sealing the lumen of the graft from its surroundings. At this point, the recipient vessel, such as an artery, is preferably still unoccluded, that is, its wall is not penetrated, and is still filled with blood flowing by.

Adhesives that may be used in the context of the present invention for various purposes, including to attach the "coattail" to, e.g., the recipient vessel wall, to seal off the lumen of the donor vessel, andor to attach the rigid member to, e.g., a graft, are general adhesives adapted for use in the human body. These include, but are not limited to, gelatin-resorcinol-formaldehyde glue, albumin-glutaraldehyde glue or enbrucilate glue, cyanoacrylate-based glues (also referred to herein as "cyanoacrylates"), polyethylene glues such as COSEAL and DURASEAL, and other glues that have sufficiently high tensile strength and low toxicologic effect. Examples of cyanoacrylate-based adhesives include, but are not limited to the ones described in U.S. Publication No. 20020065336 (Hickey et al., U.S. Ser. No. 09885,939), e.g., ETHICON OMNEX (made by CLOSURE MEDICAL), which is incorporated herein by reference in its entirety. Other adhesives such as BIOGLUE and TISSUECOL may also be used as sealants. Adhesives may include organic or inorganic agents used to assist in tissue soldering.

As described above, the recipient vessel is in most embodiment of the invention unoccluded at the time the adhesive is applied. This will essentially eliminate the risk of adhesive entering into the recipient vessel. Creating a contact plane, over a substantial part of which (e.g., about 70% per coattail or more) the adhesive may be applied, will, in addition, strengthen the contact between the donor and recipient vessel, thus either eliminating or reducing the need for additional fasteners such as clips or sutures. If additional fasteners, e.g., sutures, are used, however, the number of sutures may be reduced to one half or a quarter of, e.g., the sutures used, when neither coattails nor adhesive are employed. This reduction will shorten the time required to attach the donor to the recipient vessel, e.g., from at least half an hour to less than half an hour. The skill required to make the attachment will be reduced and, most importantly, surgery time, and thus potential complications associated with extended surgery can be reduced substantially.

As mentioned above, a preferred application of the invention is in conjunction with nonocclusive and sutureless vascular surgery, particularly vascular neurosurgery, and more preferably in conjunction with the ELANA technique and device, e.g., as described in U.S. Pat. No. 5,964,750 (Tulleken et. al.), which is incorporated herein by reference in its entirety. In certain embodiments of the invention, the rigid member used with the method and device of the present invention is a ring similar or identical to the ring used in the ELANA technique, which is placed at an end-to-side anastomosis site, either directly on the recipient vessel or preferably connected to the graft. The coattails created at the end of the graft also are preferably everted around the ring, preferably using an adhesive or mechanical measures such as, but not limited to, sutures, pins, or clips to fix their ends in place. An applicator like or similar to the catheter described in the ELANA technique can then be used to bring the graft in contact with the recipient artery and thereby avoid leakage. Vacuum suction as described in the ELANA technique also can be used to hold the graft onto the recipient artery wall while the adhesive is applied and cures, as well as for sealing off the area inside the anastomosis from introduction of uncured adhesive. Vacuum suction can also be used to dry the area to which the adhesive is applied.

In certain embodiments, the rigid member may be a ring structure, preferably a round ring, having protrusions at its surface. These protrusions may be used to facilitate or enable the attachment of the ring structure to the donor vessel andor to the tissue of the recipient vessel. These protrusions may further reduce or even eliminate the need for sutures or similar to attach a donor vessel to a recipient vessel. This will reduce time and thus reduce the risks associated with prolonged surgery. In certain embodiments of the invention, the time to attach a donor to a recipient vessel will, when the rigid member having protrusions is employed, be reduced to 50%, 25%, or even 5% of the general time required for such an attachment. This translates into an attachment time of less than half an hour or less than 10 minutes. In embodiments in which no suturing is performed and the attachment method only involves use of a ring with protrusions in combination with adhesive applied to andor between the "coattails" of the donor vessel as discussed above, the attachment time may be reduced to less than 5 minutes, less than 4 minutes, less than 3 minutes or less than 2 minutes, depending on the experience of the surgeon.

As the person skilled in the art will appreciate, the protrusions will generally be configured to (1) allow for ease of attachment of the donor to the recipient vessel and (2) securely fasten the vessels to each other. The first of these functions will generally advocate a relatively simple design, while the second requires enough complexity in the design of the protrusions to prevent a sliding off the vessels in the short-andor long-term. In addition, the protrusions will have to conform to certain size requirements so that at least two vessel walls comfortably fit onto them.

The protrusions have generally pointed tips, in which case they are also referred to herein as "protruding pointed structures" which, in turn, may also just be called spikes, needles or, in most instances, pins. When these "protruding pointed structures" have a bent structure they may also be referred to herein as hooks or hooked protrusions, but also as hooked spikes, hooked needles, hooked pins, in particular when the hooks has no curved structure. In certain embodiment, the protrusions, especially hooked protrusions, extend at least in part along a plane defined by the ring structure, including above or below this plane.

A rigid member with at least one or more protrusions, may, in a more preferred embodiment, be used in place of, or in addition to, other measures, including, but not limited to, sutures, staples, clips, or adhesive, to attach, e.g., the graft onto a donor vessel such as an artery. Pointed tips of the protruding pointed structures may allow for easier penetration of, or fixation in tissue. In one preferred embodiment there may be two protrusions facing away from the center of a ring structure, e.g. in essentially opposing directions. The protrusion may in this and other embodiments of the invention be arranged symmetrically (at 180°) or may be slightly offset against each other, e.g., by up to 20° in each direction including up to 15°, 10°, or 5°. The protrusions, also in this and other embodiments of the invention, may at least in a part proximate to the ring, extend out of the plane of the ring structure at an angle of more than 0° and about 90°, such as about 15° to about 45°, but are preferably in said plane and then optionally curve so that they point at the protrusion's tip in a direction which encloses an angle with said plane of the ring structure of between about 30° into either direction of the plane. However, in certain preferred embodiments all parts of the protrusion are in the plane of the ring structure.

Figure 2:
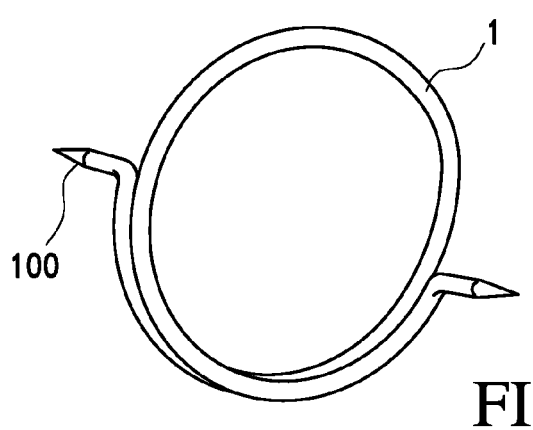
FIG. 2 shows one embodiment of the rigid member of the present invention.

A simple example of an embodiment of the present invention using two protrusions 100 is shown in FIG. 2. The length of such a protrusion, which in FIG. 2 is shown as a pin, is preferably about 1-5 times the expected recipient vessel wall thickness. Thus, in total each hook is about 0.2 mm to about 2 mm, preferably about 1 mm in length for large intracerebral arteries having a wall thickness of about 200 to about 400 µm. In FIG. 2, the ring is made of a wire with sharpened ends rolled up to form a ring. Alternatively, a ring structure could have sharp hooks or pins attached.

Other preferred embodiments of rigid members with two protrusions are shown herein and will be discussed in greater detail below.

In certain embodiments, the rigid member may have at least three, four, five, six, seven, eight, or more protruding pointed structures extending from the rigid member. Generally, the protruding pointed structures, of the rigid member can point in a number of different directions relative to the rigid member, so long as they perform the function of adequately attaching the graft containing the rigid member to the target tissue. The protrusions may be conceptually subdivided into different regions. One of these regions is the region proximate to the rigid member ("proximal region"), a second is the distal part or tip of the protrusion and the third one is the part of the protrusion between these ends ("midsection"), the latter of which is generally the longest part of the protrusion. As indicated above, the protrusion can extend, at least initially, i.e., at the proximate region, either in or outside the plane, which is preferably defined by a ring structure, of the rigid member. If it extends outside the plane of the rigid member, it preferably does so at an angle of between more than 0° and about 120°, preferably about 90°, and may then (gradually or abruptly) curve into a plane, which is substantially parallel to the plane of the rigid member. The curve may be at such a place in the protrusion as to provide sufficient distance between the rigid member and the curvature to hold about one or two layers of tissue (See hooked protrusion in FIGS. 3A and 3B, but also FIGS. 4A and 4B). For a typical vessel wall, this distance is about 0.05 mm to about 2 mm, preferably about 0.2 to about 0.8 mm. The straight protrusion 100 in FIGS. 3A and 3B extends as a whole at an angle of 90° from the plane of the rigid structure.

Figure 3A:
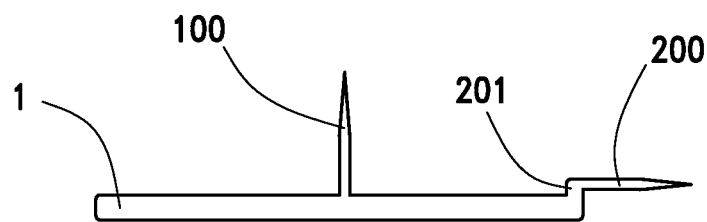
FIGS. 3A and 3B depict another embodiment of the rigid member prior to (3A) and after full assembly (3B).
Figure 3B:
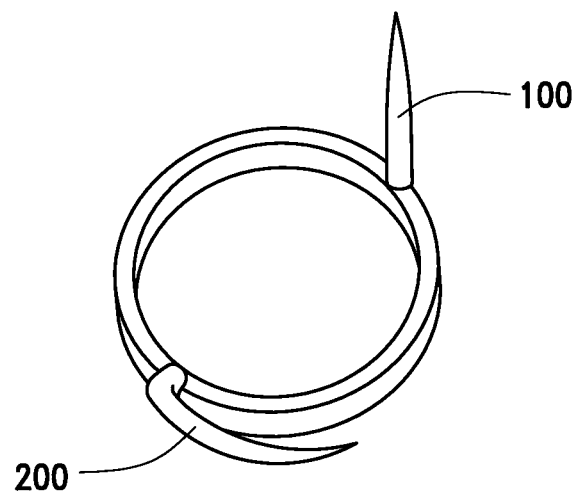

The protrusions may be attached on the lower surface of the rigid member 1 as shown for pin 100 in FIGS. 3A and 3B, which both show the bottom of the ring at the top of the Figure. To adequately hold onto tissue, such as that of an artery, in one embodiment of the invention, at least one of the protrusions of the rigid member, such as a ring structure, extends at least in part preferably in a direction essentially parallel to the plane defined by the rigid member by about 1/100 to about 1/1 of the outer diameter of the rigid member, preferably between about 1/25 and about 1/4 of the diameter, and more preferably about 1/10 to about 20 times the thicknessdiameter of the material of the rigid member, and even more preferably between 1/2 and 4 times the thicknessdiameter of the material of the rigid member (i.e., preferably about 0.1 to about 1 mm to connect vessel walls) (See also embodiment shown in FIGS. 4A-4C). In certain embodiments of the invention, the hooked protrusion is preferably located underneath the ring. In the embodiment shown in FIG. 3B, the proximal portion 201 of the hook 200 protrudes perpendicularly from the plane of the ring for about 0.1-0.5 mm to form a strut. The straight pin 100 is here shown in FIGS. 3A and 3B as pointing perpendicular to the plane of the ring, but will be in many embodiments be within the plane of the ring. However, preferably the straight pin is within the plane of the ring. Nonetheless, variations are possible, including the pin 100 pointing above or below (FIGS. 3A and 3B) the plane of the ring. FIG. 3B shows a finished embodiment of the ring, while FIG. 3A shows a precursor in the manufacture of the ring shown in FIG. 3B.

In certain embodiments, the rigid member 1, preferably a ring structure, may be equipped with four protruding pointed structures.

Figure 4A:
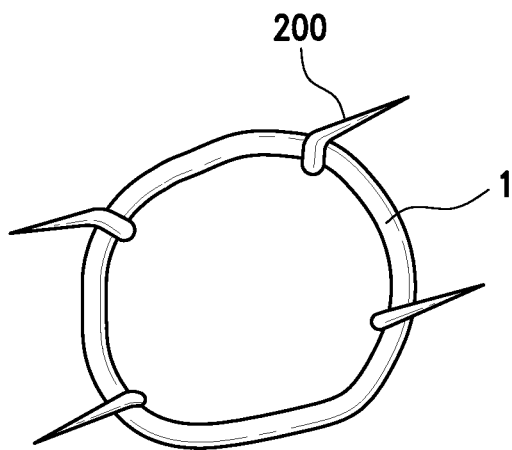
FIGS. 4A to 4C depict another embodiment of the rigid member of the present invention prior (4A) and after (4B, 4C) engagement with a donor vessel. In 4C, an applicator is shown in the lumen of the donor vessel.
Figure 4B:
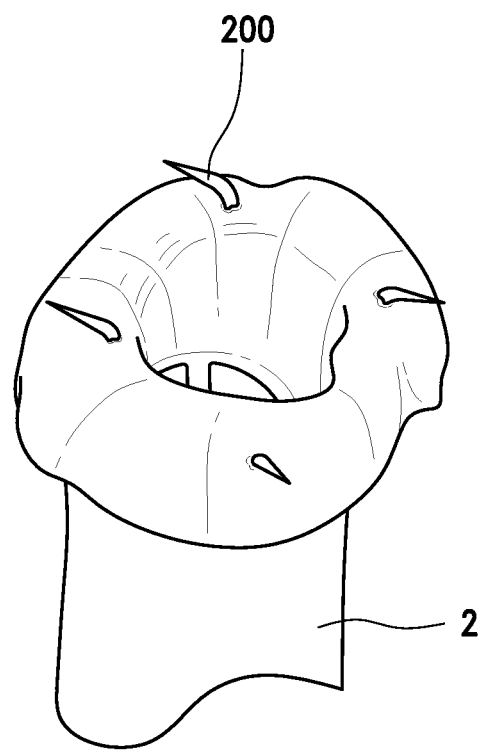

An example of a possible direction of the protrusions 200 outward from the rigid member 1 of such a four protrusion embodiment is shown in FIG. 4A. Protrusions can be located closer together along the rigid member 1 by, for example, bending the protrusions inward towards the rigid member. In this way the wall of the artery 10 between the attachment points of the pins on the rigid member is stretched. FIGS. 4A and 4B show embodiments in which the protrusions 200 are arranged in pairs of two that are "substantially" parallel to each other. In the context of the present invention, the terms "essentially" and "substantially" are associated with a number of terms that indicate direction. These terms are used to describe a general orientation of, e.g., the protrusions and will also include the "perfect" direction. Thus, the term "substantially parallel protrusion" includes a perfectly parallel protrusion. However, as the person skilled in the art will appreciate, deviations of these perfect alignments are common and are part of the present invention. The degree of deviation permissible may, be, e.g., a function of the material used, including its thickness andor the process involved in producing the protrusions. Often during use, the orientation of, e.g., a protrusion may further change due to deformation. Any degree of deviation from the "perfect" orientation that is acceptable for clinical use is within the scope of the present invention. Generally, this will be any orientation that still allows attachment to a tissue, without damaging this tissue in a way that would cause leakage or instability of the connection in which the rigid structure is employed.

As discussed above, the wall of the graft may be cut at one or more positions, including two, three, four, five, six, seven, eight, or more positions, e.g., in as many positions as there are pins or other pointed protrusions, by an incision starting at the end of the graft 3 nearest the rigid member and, preferably, proceeding substantially in an axial direction towards the rigid member 1.

Such incision(s) preferably end before the rigid member 1, preferably at a distance of between about 1/2 and about 2 times, more preferably about 1 time, the wall thickness of the tubular member or graft.

Figure 4C:
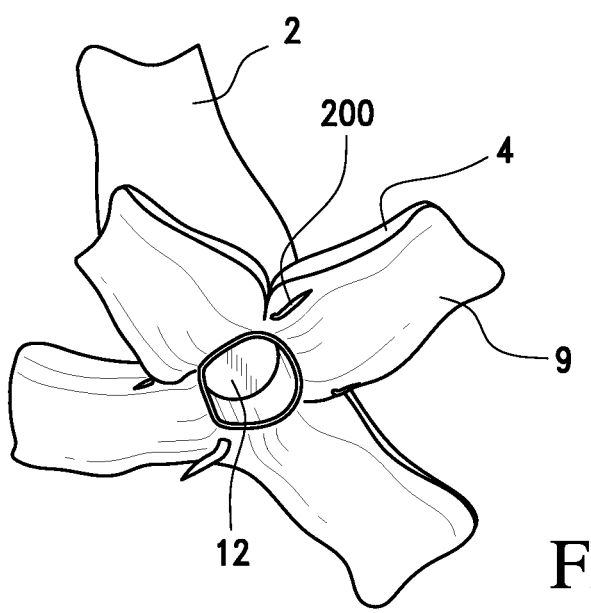

Preferably an even number of such incisions are made at essentially symmetrical positions along the wall circumference of the graft, i.e., for any one cut, there is a corresponding cut at the position of maximum distance around the circumference of the graft, as preferably measured at the position of the rigid member, in such a way that the incisions separate the wall into regions, which like coattails can be lifted away from the axis of the graft. These coattails 4 provide a larger surface 9 with which to make contact 8 with the artery or other vessel 5. In FIG. 4C, an example of a graft is shown having four incisions and thus four coattails 4. The rigid member 1 also is shown attached to the graft, and in the lumen of the graft 7 an applicator 12 is visible. The coattails 4 may then be folded back against the graft.

Figure 5A:
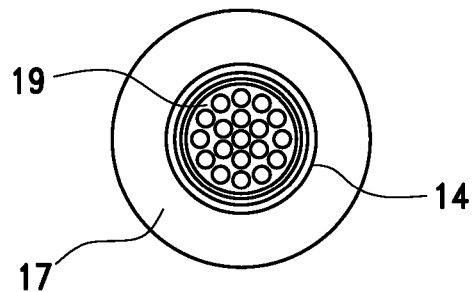
FIGS. 5A and 5B show a preferred applicator that may be used in the context of the invention.
Figure 5B:
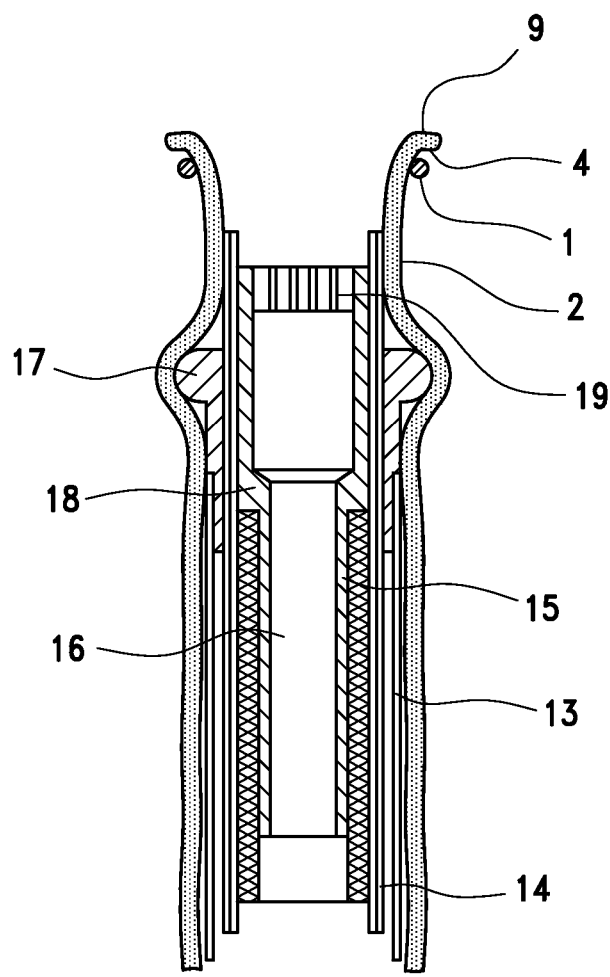
Figure 6A:
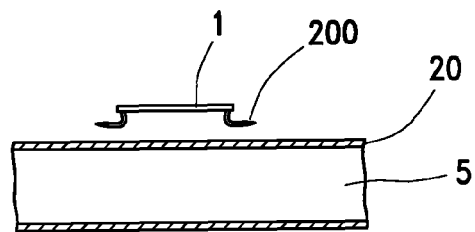
FIGS. 6A to 6G depict stages in the attachment of a rigid structure, such as the one shown in FIG. 4A, having a donor vessel attached (not shown) to a recipient vessel.
Figure 6B:
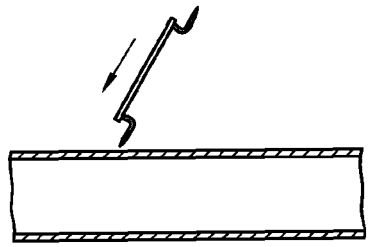
Figure 6C:
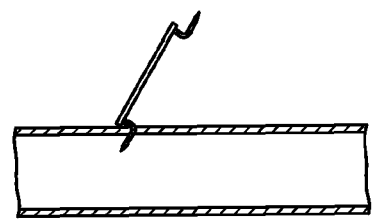
Figure 6D:
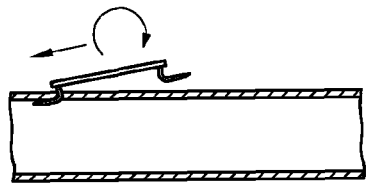
Figure 6E:
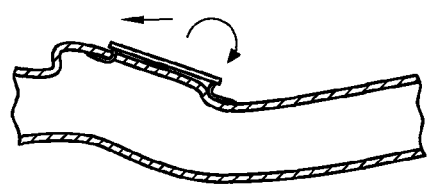
Figure 6F:
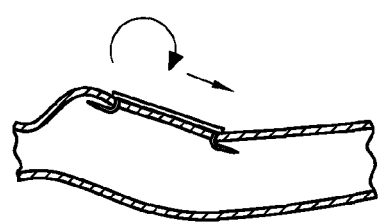
Figure 6G:
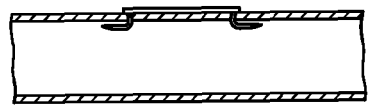

FIGS. 5A and 5B show top and front cross sectional representations of the distal region of a preferred applicator 12. The applicator is a laser catheter which surrounded by a casing 13, which meets the typical demands for use in the medical field, such as easy sterilization, high flexibility, and material compatibility. The outer casing 13 surrounds the ring-shaped arrangement of the optical fibers 14 which are disposed in two layersin two concentric circles in the preferred embodiment shown in FIG. 5B. This can also be seen in the top view of the tip of the laser catheter of FIG. 5A. In connection with an inner tube-shaped casing 15, a hollow channel 16 is surrounded, which is joined at its proximal end to a low pressure source (not shown in FIG. 5). At the tip of the distal region of the invented laser catheter, there is provided an outer circumference-widening element 17, which in the preferred embodiment has an atraumatic ring-shaped cross-section, with a straight stop edge in the direction of the distal end. The dimensioning of the outer-circumference widening element 17 should be such that the outer circumference of the element can fit through the lumen of the vessel 2 through which the laser catheter is to be guided. In this way, it is ensured that the catheter tip is centered inside the vessel channel in a self-guiding manner by resting with its circumference on the inside area of the vessel channel.

In the direction of the distal end of the laser catheter tip, the ring-shaped optical fibers 14 project beyond the plane of the widening element 16. The optical fibers 14 for their part surround a holding means 18, which represents on the proximal end a termination for the inner casing 15 but which, in particular provides, a holding device for a perforated member 19, which leads the low pressure prevailing inside the hollow channel 16 to the top. A top view of the laser catheter tip in FIG. 5A shows an advantageous arrangement of perforation boreholes, which are disposed in concentric circles. The top view representation also shows the circumference area of the element 17 widening the outer circumference of the laser catheter.

The typical dimensions of the laser catheter are scaled as follows: the outer diameter of the casing 1 of the laser catheter is 2.2 mm, whereas the diameter at the distal end region increases by means of element 5 to 3 mm. The optical fibers usually project 1.5 mm out of element 5 and have an outer diameter of 1.9 mm. At a distance of about 0.5 mm from the light exit area, the perforated member 7 is set inside the optical fibers 2. In the form depicted in FIG. 5, the perforated member 7 is provided with eighteen boreholes each having a diameter of 0.2 mm. However, the described sizes have to be adapted to the size conditions given by the dimensions of the vessel.

The graft 2 and rigid member 1 can then be attached to the artery or other vessel. This can be done with simple and relatively small movements.

FIGS. 6A-F show a lateral view of a sequence of attaching a first tubular member to a second tubular member 5 using the embodiment of the invention shown, e.g., in FIGS. 4A-C. As can be seen in 6A, the figure only shows the recipient vessel 5 and two protrusions 200 as seen from a lateral view. In practice the rigid member will be attached to the graft 2 as shown, e.g., in FIG. 4B and may also include an applicator 12 as shown in FIG. 4C and FIGS. 5A and 5B. Generally, the coattails 4 shown in FIG. 4C would be folded back, again unfolded and attached to the recipient vessel walls after the attachment process shown in FIGS. 6A-F is completed. As can be seen in 6B and C, a downward movement at an angle will allow two protrusions 200, here the ones shown on the left-hand side, to penetrate the recipient vessel wall. As shown in 6D and E, a rotational movement around the axis of the inserted protrusions combined with a movement substantially along the axis of the recipient vessel 5 to further engage the inserted protrusions 200 with the lumen of the recipient vessel 5, will, in view of the elasticity of the vessel allow insertion of the protrusions 200 located at the opposite end of the ring structure, here depicted on the left side, at which point, as shown in 6F, the movement substantially parallel to the axis of the recipient vessel is reversed to ensure full engagement of these protrusions 200, which results in a full attachment, as shown in 6G. As indicated in 6E and 6F, the recipient vessel 5 will be subjected to considerable stretching, which renders this embodiment of the invention primarily useful in the context of recipient vessels that can readily withstand such stretching forces.

The rigid member 1 does not only serve as to join vessels, but has the further advantage that it may act as a stabilizing member to help shape and/or define the form of a connection before and/or during the attachment process, as well as possibly after the attachment process is completed. As indicated in FIGS. 6D-G, the rigid member 1 can add to and/or define the level of tension on one or more of the tissues joined. Furthermore, the rigid member 1 may help reduce or remove strain on the adhesive bonds between the tissues, while the adhesive is curing and/or thereafter and prevent the coattails from becoming separated from the artery wall due to blood pressure. Furthermore, the rigid member may act as a stopping device that presses the graft wall against the artery wall, either when fixed with clips or sutures, or when applied with force using an applicator or manually with forceps or the like.

In a preferred embodiment, the rigid member, which is preferably a ring, is made to be more rigid than the vessel wall. The rigid member can, e.g., be made using metal or ceramic and sintered materials, as well as certain plastics or adhesives. Metals can be used in certain embodiments, as they are, among other things, fairly rigid and durable, even in thin layers, while still having a flexibility that can be precisely determined and being easy to manufacture. Possible metals include the metals that are widely used as implant materials, such as stainless steel, platinum, titanium, NiTi alloys, and CoCr alloys. Many of these alloys are proven to be biocompatible. In another preferred embodiment of the invention, the rigid member contains or is made of bio-degradable or bio-absorbable materials. Additionally, plastic materials including acrylate and cured or still-curing adhesives such as cyanoacrylate and other glues described above also can be used for manufacturing the rigid member. Furthermore, plastic materials have the advantage of being durable and available in wide varieties of flexibility, stiffness, and durability. Plastics, like many ceramics and sintered materials and selected metals, are also well compatible with MRI, PET, or CT scans and angiograms performed post-operation.

In a variety of other preferred embodiments of the invention, the rigid member of the invention is equipped with a combination of straight and hooked protruding pointed structures, which are also in the following description of the Figures just referred to as "pin" and "hook" or similar, respectively, without limiting the scope of the invention.

Figure 7:
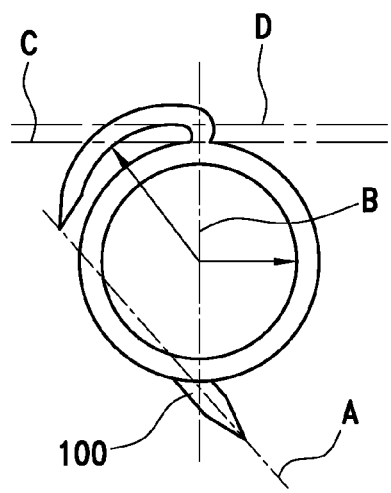
FIG. 7 shows preferred rigid member according to the invention, having a hook and a pin as protruding pointed structures.

The pin may be arranged at the ring to extend perpendicular (see FIGS. 3A and 3B), but generally extend, e.g., radially, but generally at an angle from the ring in the plane defined by the ring structure as shown in FIG. 7, while the hook extends at its midsection, tip and here even at its proximal portion, along the plane defined by the ring structure substantially along the circumference of the ring. Attachment of the graft, whose open end has been fastened to the ring structure, to the recipient vessel via this type of rigid member comprising straight pinhooked pin combinations shown usually commences with the full insertion of the straight pin into the wall of the recipient vessel. The insertion site then forms a pivot point. After the hook is inserted, the ring structure is turned around this pivot point to ensure full engagement of the hook with the vessel wall of the recipient vessel. At least the midsection of the hook is in certain embodiments located in a plane defined by the ring but underneath the ring, a preferred embodiment of which is shown in FIG. 3B. At its proximal portion, the hook preferably protrudes perpendicularly from the plane of the ring about 0.1-0.5 mm forming a strut (e.g., FIG. 3A). The straight pin may points outward in the same plane as the ring, but variations of this configuration are possible and desirable, including the pin pointing, as a whole or only, e.g., at its tip (thus becoming a "hooked pin", an configuration that will be discussed in detail later on), above or below the plane of the ring. FIG. 3B shows a finished embodiment of the ring, while FIG. 3A shows a precursor in the manufacture of the ring shown in FIG. 3B.

Figure 8A:
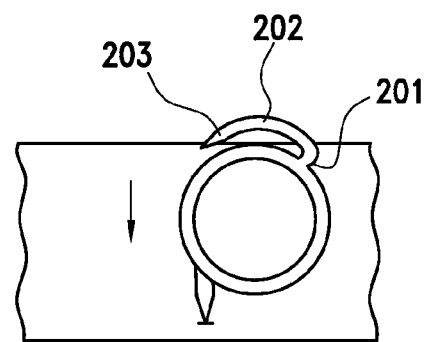
FIGS. 8A to 8E depict stages in the attachment of the rigid member depicted in FIG. 7, having a donor vessel attached (not shown) to a recipient vessel.
Figure 8B:
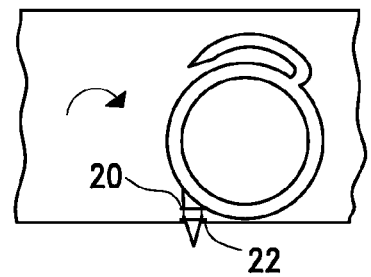
Figure 8C:
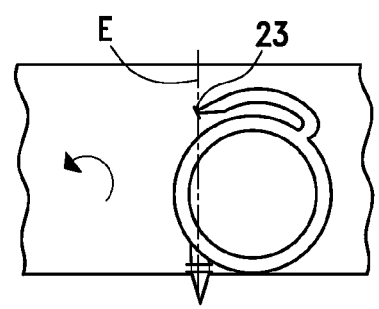
Figure 8D:
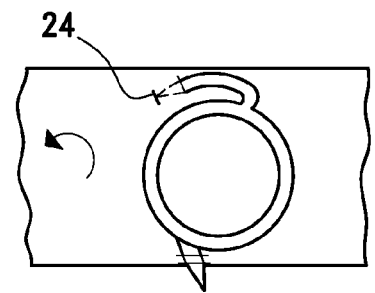
Figure 8E:
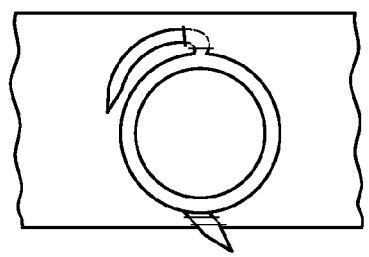

A particularly preferred embodiment of the ring structure is shown in FIG. 7 and a way of inserting it into a recipient vessel is shown in FIGS. 8A-E. Here, the midsection and tip of one of said protrusions (hook) extends substantially parallel to the outer circumference of the ring structure, wherein another protrusion (pin) extends essentially straight from said ring structure along a secant [A] of said ring structure extending from a tip of the hook to an attachment point of pin at the ring. Stated differently, the pin extends at an angle from the axis [B] of the ring structure through its attachment point and an angle, which is here about 45° and defined by the above secant. However, other angles relative either side of said axis [B] are also within the scope of the present invention, such as, about 80°, about 70°, about 60°, about 50°, about 40°, about 30°, about 20°, or about 10°. The hook is generally longer than the pin, e.g., at least about 50%, about 60%, about 70%, about 80%, about 90%, or about 100% longer than the pin, which may have a length of about 10% to about 50%, preferably about 10% to about 25%, of the outer circumference of the ring structure. In certain embodiments, these measurements apply to the midsection of the hook only. The distance between the ring and the hook is, e.g., at the midsection of the hook, generally about 50% to about 200% of a typical thickness of a recipient vessel wall, e.g. about 0.2 mm. The proximal portion of the hook which has, in the embodiment shown, the form of a strut extending, e.g., 0.2 mm radially from the ring structure, i.e., at an angle of about 90° from a tangent [C] of the ring through the hook's attachment point (along axis [B]), defines this distance. In FIG. 7, the strut is also shown to extend radially outward in the plane defined by the ring structure. However, as the person skilled in the art will appreciate, the strut can be attached to the ring at differing angles. Accordingly, rather than extending radially, the strut may enclose an angle of up to about 45°, up about 30°, up to about 20°, up about 10° relative to either side of the axis [B]. Alternatively or additionally, the strut may extend out of the plane defined by the ring structure and may enclose an angle of, e.g., up to about 90° (FIGS. 3A and 3B), up about 45°, up to about 30°, up to about 20°, up about 10° either above or below this plane. These configurations are, as the person skilled in the art will appreciate, also possible with other embodiments having struts, such as the one shown in FIGS. 3A and 3B, as well as with embodiments in which the region proximal to the ring structure does not have a strut structure such as the embodiments shown in FIGS. 17A and 17B. Similarly, while, in a preferred embodiment, at least the midsection of the hook extends substantially parallel to the outer circumference of the ring structures including, depending, e.g., on the orientation of the strut, slightly above or below the plane defined by the ring structure, other configurations are within the scope of the present invention. E.g., the midsection can enclose an angle with the parallel [D] to tangent [C] ([D] traverses, as shown, the point in which the strut becomes the midsection of the hook) and which defines the direction of the midsection different from the about 0° depicted, e.g., of up to 90°, at which point the midsection extends substantially radially from the ring structure, but preferably, up to about 45°, up to about 30°, up to about 20°, up to about 10° or up to about 5°. The graft (not shown) may be attached to the ring structure via a couple of simple attachments steps which will also be discussed below. Attachment to the recipient vessel is schematically depicted in FIGS. 8A-E, which illustrates the insertion process as a top view and, for simplicity's sake, only shows the ring and the recipient vessel. An applicator 12 aids, in a preferred embodiment, in the attachment. As shown in FIG. 8A, the pin is first caused to puncture the wall of the recipient vessel in the perpendicular [E] to the axis of the recipient vessel so that the pin either does not enter the lumen of the recipient vessel or that its point of entrance 21 and its point of exit 22 are as close as possible as shown in FIG. 8B. The ring, preferably via an applicator (not shown), is, as shown in FIG. 8C, rotated so that the tip of the hook 203 is positioned exactly opposite the point 23 where the pin penetrated the recipient wall 20, wherein the axis [E] perpendicular to the axis of the recipient vessel serves again as reference axis. The ring is then rotated further so that the tip 203 of the hook penetrates the wall of the recipient vessel as shown in FIG. 8D. Further rotation in this direction ensures that the hook enters and, preferably exits, e.g., at point 24, the lumen of the recipient vessel, while the pin further penetrates the vessel wall as shown in FIG. 8E.

Figure 9:
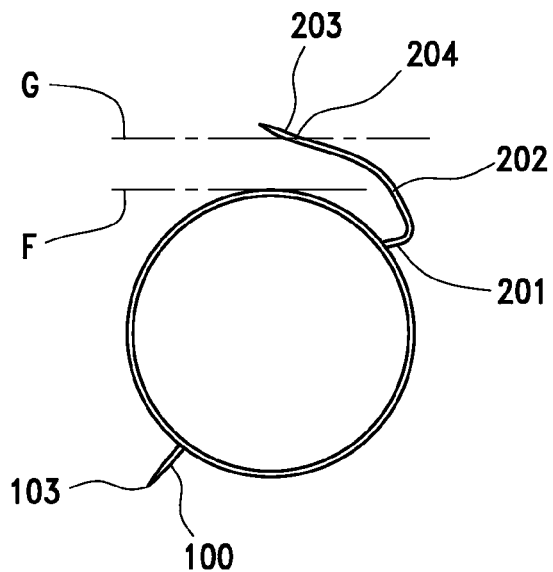
FIG. 9 shows another preferred rigid member according to the invention, having a hook and a pin as protruding pointed structures.
Figure 10A:
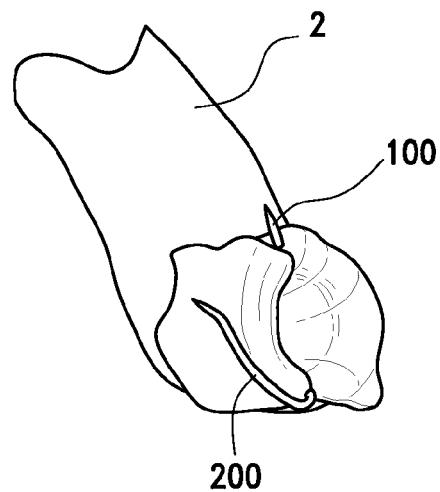
FIGS. 10A and 10B show the rigid member of FIG. 9 after engagement with the donor vessel. In 10B an applicator is shown in the lumen of the donor vessel.
Figure 10B:
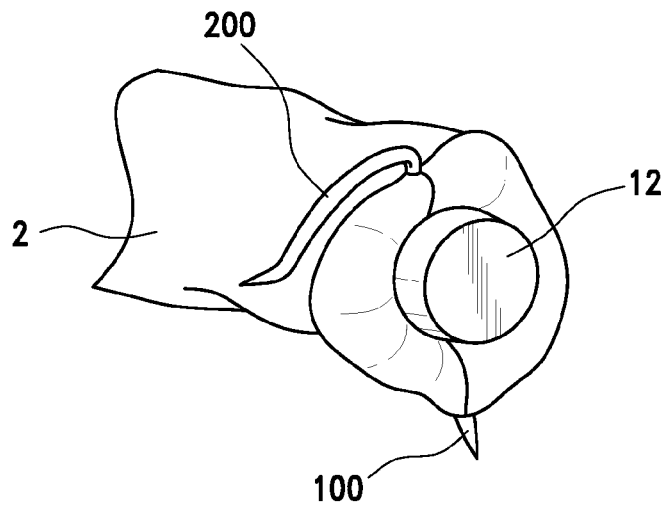

Another hookpin embodiment is shown schematically in FIG. 9. In FIGS. 10A and 10B, this embodiment is attached to a graft 2, in 10A without an applicator, and in 10B with an applicator 12 inserted into the lumen of the graft.

In the embodiment shown in FIGS. 10A and 10B, the ring structure, the pin, and the hook are also preferably in substantially one plane. The hook as a whole has also a preferred length of about 25% of the circumference of the ring, and preferably has an ultra sharp tip, which many be about 0.1 mm to about 0.3 mm in length, preferably about 0.2 mm in length. The hook also is preferably connected to the ring by a strut having a preferred length of about 0.1 mm to about 0.3 mm, most preferably of about 0.2 mm. The strut 201 is shown to deviated from a radial orientation from the plane by about 10° and in substantially the same plane as the ring. Alternative configurations, e.g., as described in the context of the embodiment shown in FIG. 7 are possible and within the scope of the present invention. The hook may, similarly to the embodiment shown in FIG. 7, at least in part, here in the midsection of the protrusion, extend substantially parallel to the ring structure, but does here, at its tip (proximal of its attachment point to the ring) extend outwards. As indicated in FIG. 9, the midsection of the hook, which preferably is made of the same material as the ring and the strut, extends from the end of the strut at an angle of slightly more than about 90°, but then runs substantially parallel to the ring's circumference, preferably at a distance of about 0.2 mm from the ring (i.e., which corresponds to the length of the strut). The tip 203 of the hook points in certain preferred embodiments away from the ring, as also shown in FIG. 9. The tip may define an angle with a parallel [G] of a tangent [F] of the ring, wherein the tangent [F] touches the ring at the point 204 that defines the transition from midsection 202 to the tip 203 of the protrusion. Alternatively or additionally, the tip of the hook may define an angle with either side of the plane defined by the ring structure. Either of theses angles may be up to about 90°, up to about 45°, preferably up to about 30°, up to about 20°, up to about 10° or up to about 5°. On the opposite side of the ring, here directly opposite, is located a straight pin 100 pointing radially away from, and in the plane of the ring as opposed to the embodiment depicted in FIG. 7. The pin may, however, be somewhat offset from this directly opposite position, e.g., by about 20° (compare FIGS. 17A and 17B). Other deviations from a perfect 180° alignment are possible, such as about 10°, about 30°, or about 45° and within the scope of the present invention. In the embodiment shown, the tip 203 of the hook terminates about 30° offset of the attachment point of the pin.

This pin 100 has in certain preferred embodiments an ultra sharp tip 103, which also may bends slightly upwarddownwards at its end creating a hooked pin. The tip may have an orientation relative to the ring structure as, e.g., described above for the tip of the hook. In certain embodiment of the invention, there may be two or more pins arranged at the ring (compare FIGS. 17A and 17B). The tip 103 of the pin may here, as well as in the context of other embodiments of the invention such as the one shown in FIG. 7, when assuming the conformation of a hooked pinhook point in a variety of orientations in space including all orientations discussed herein in context of hooks. Different examples of these embodiments are depicted in FIGS. 11 to 16.

The attachment of the graft to the ring can be achieved similarly as in other embodiments of the ring structure comprising straight andor hooked protrusions, wherein the straight protrusion may, as discussed above, also be a hooked pinhook. However, processes that may be used to attach the ring structure to the graft 2 as shown in FIGS. 10A and 10B will be explained for illustrative purposes: The sleeve at the end of the graft 2, once cut, is everted around the ring as shown in FIG. 10A. The graft 2 is fixed to the ring either by puncturing the wall of the vessel with the pin and hook, or by suturing the donor vessel to the ring using stitches, preferably two, which pass through the wall of the donor vessel at the ends of the cuts in the coattail next to the ring, and which wrap around the ring at the sites of both the strut of the hook 200 and the pin 100. In this way, the hook 200 is visible over its full length, as shown in FIGS. 10A and 10B.

The use of the hookpin combination as shown in FIG. 9 further promotes the movement of the direction of the hook as shown in FIGS. 8D and 8E, in which the hook, shortly after entering the lumen at point 23, then penetrates the wall again from inside to the outside at 24. This movement is followed by pushing the hook over its full length through. When the strut 201 reaches the point of entry of the hook, the wall of the recipient vessel is pulled over the strut spontaneously by tension present in the vessel wall as shown in FIG. 8E. The hook remains completely outside the recipient vessel except for a part of the strut, which is located in the lumen of the recipient vessel between entry 23 and exit point 24 to the hook. The coattail 4 of the donor vessel, which is located between the ring and the hook during the application procedure (see, e.g., FIG. 10A), can now easily be repositioned to a position between the hook and the outside of the recipient wall. Direct contact between the coattail and the surface of the recipient wall can thus be established, and the procedure can advance to the application of the glue. Both the embodiment depicted in FIG. 7 as well as the embodiment depicted in FIG. 9 have the advantage that the hook is fully visible while connecting the donor vessel to the recipient vessel. This means that the puncturing of the tip of the hook into the recipient vessel at 23 can be visually controlled. In this way, the optimal puncture spot (which preferably is exactly opposite the point 21 where the pin of the ring has punctured the recipient wall) can be determined. In addition, the embodiment shown in FIG. 9 further ensures that the tip of the hook can readily exit the recipient vessel wall in a short distance from its entry point, preferably at a distance of about 0.1 mm to about 0.2 mm from the entry point at point 24. In addition, while the hook is pushed through the small perforation in the recipient vessel wall, this embodiment allows one to visually monitor when the strut of the hook is reached and the ring becomes firmly fixed to the recipient vessel. One of the main advantages of the embodiments shown in FIGS. 7 and 9 is that entire midsection 202 and tip 203 of the hook is outside the recipient artery, and thus no foreign material is introduced into the lumen of that artery. The distance between the entry (21, 23) and exit points (22, 24) of the pin 100 andor the hook 200 at the recipient wall is so small that this procedure is really no different from applying a simple suture.

Furthermore, the different configurations of the rigid member comprising protrusions, may, upon attachment of the rigid member at the recipient vessel, put the wall of the recipient vessel between the points or areas of attachment under tension. For example, the recipient vessel wall may, between two attachment pointsareas, be stretched about 5%, up to about 10%, up to about 20%, up to about 30%, up to about 40% or more, but preferably between about 10% and about 30%, even more preferably between about 10% and about 20%. If, for example, the two protruding pointed structures of the embodiment shown in FIG. 7, are inserted into a recipient vessel according to the scheme shown in FIGS. 8A to 8E, the wall of the recipient vessel will be stretched by about 10%. This is because the very tips of the protrusions defining the points of entry into the recipient vessel (21, 23) are separated by a distance of 3.9 cm, while the recipient vessel wall will, on the outer circumference of the ring at the proximal parts of the two protruding pointed structures as shown in FIG. 8E, will come to rest at a shorter distance of, in this example, about 3.5 cm. As the person skilled in the art will appreciate the tension will vary with the specific configuration of the protruding pointed structures and the ring circumference.

This stretching of the recipient vessel may have one or more of a number of advantages, including, but not limited to, preventing the rigid member from disengaging from the recipient vessel, simplifying subsequent suturing andor cutting of the recipient vessel which can more readily done when the area in question is under tension andor reducing the risk of damage to the interior wall tissue of the recipient vessel. Without the tension created inherently by configuration of the ring structureprotruding pointed structures, the rigid member is simply pressed only the recipient wall prior to suturing andor cutting to create a similar effect. This may, however, flatten the vessel and thus bring the opposing wall of the recipient vessel close to the point where the connection between donor and recipient vessel will be made, thus increasing the likelihood that, e.g., a laser cutting the recipient vessel will also reach this opposing wall of the vessel and damage it.

FIGS. 11 to 16 depict various preferred embodiments of the ring structure described above and that can be used according to the scheme shown in FIG. 8. These figures demonstrate that what is shown in FIGS. 7 and 8A-8E as a pin can be configured as a hooked pinhook. These changes will generally not negatively interfere with the attachment process shown in FIGS. 8A-8E.

Figure 11A:
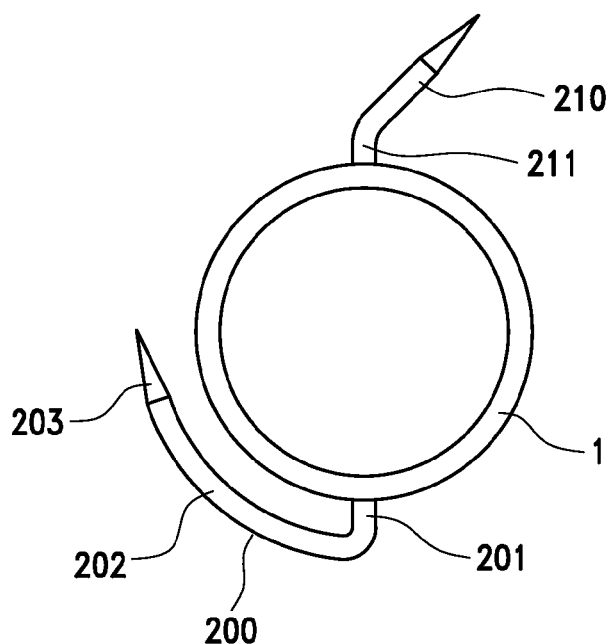
FIGS. 11A and 11B are a top and lateral view, respectively, of another preferred rigid member having a hook and a hooked pin as protruding pointed structures.
Figure 11B:
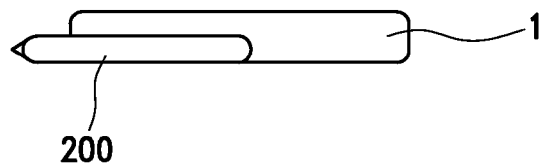

FIG. 11A is a top view of a 11B is a side view of one preferred embodiment of the invention which is similar to the configuration in FIG. 7, but the pin has been replaced by a hooked pin 210 which has a strut 211 and the hook 200 is somewhat extended to extend over the ¼ of the circumference of the ring. As can be seen in FIG. 11B, in the embodiment shown the ring structure 1 is higher than the protrusions 200 (shown). However, the ring might also be a wire and can have the form of a spiral with 1½ windings ending in the pins (compare FIG. 2).

Figure 12A:
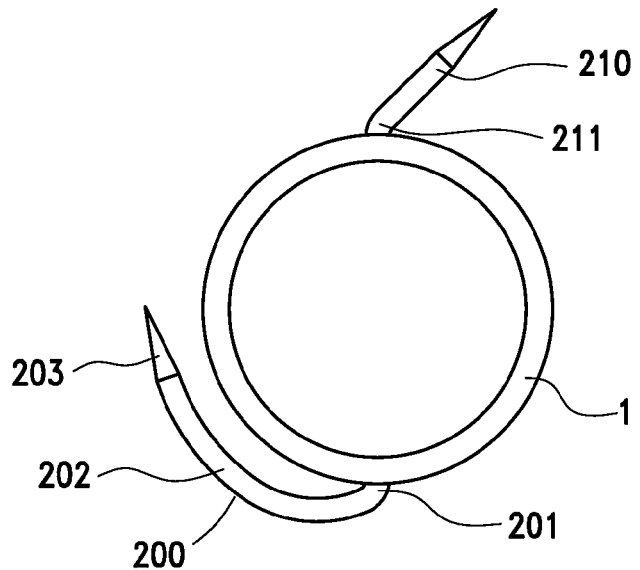
FIGS. 12A and 12B are a top and lateral view, respectively, of another preferred rigid member having a hook and a hooked pin as protruding pointed structures having a very short strut as a proximal portion of the protruding pointed structures.
Figure 12B:
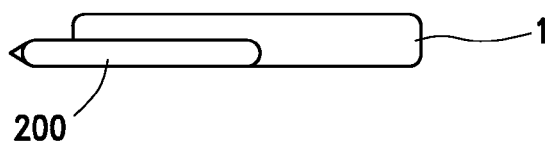

FIG. 12A is a top view of a 12B is a side view of another preferred embodiment of the invention. This embodiment is similar to the one in FIGS. 11A and 11B but only comprises a minimal radially outward extending strut 201 at the hook and essentially none at the hooked pin 211.

Figure 13A:
FIGS. 13A, 13B and 13C are a sectional, top and lateral view, respectively, of another preferred rigid member having two hooks of differing length as protruding pointed structures each of which extending substantially parallel to the circumference of the rigid member.
Figure 13B:
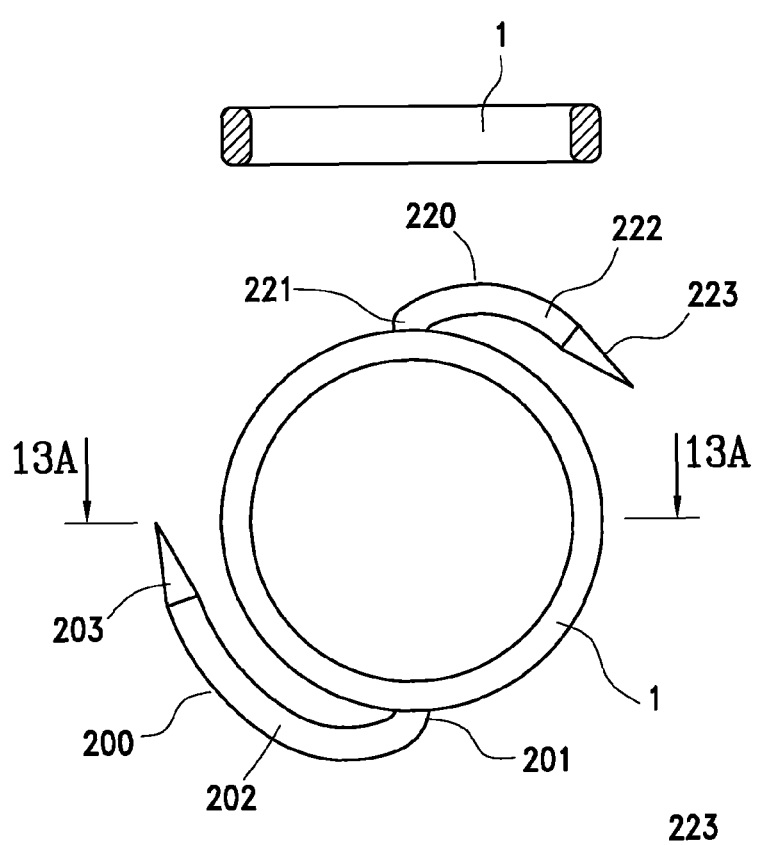
Figure 13C:
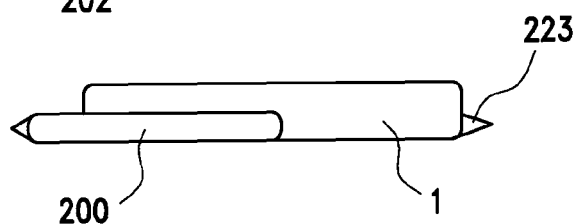

FIG. 13A is a cross-section through the middle of the ring showing a solid ring structure, while FIG. 13B is a top view of a 13C is a side view of another preferred embodiment of the ring structure comprising two hooks (200, 220). Both hooks have only very short radially outward extending struts (201, 221). One of the hooks 200, extends parallel around about a quarter of the ring's circumference, the second hook 220 is only about half the length of the first hook. As the person skilled in the art will appreciate and explained in detail above other two hook configurations are possible. This configuration of the second hook (220) may stabilize the engagement of this protrusion which may serve the function of the straight pin shown in FIGS. 8A to 8E.

Figure 14A:
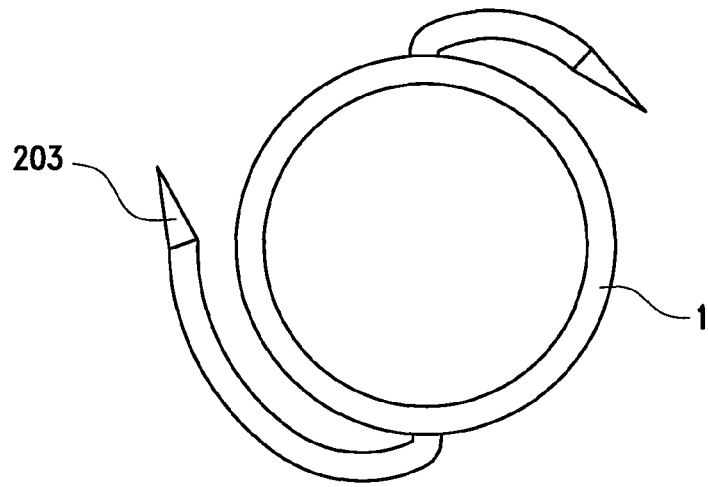
FIGS. 14A and 14B are a top and lateral view, respectively, of another preferred rigid member having two hooks of differing length as protruding pointed structures each of which extending substantially parallel to the circumference of the rigid member. The longer of the two hooks is somewhat extended than the respective hook in the embodiment shown in FIGS. 13B and 13C.
Figure 14B:
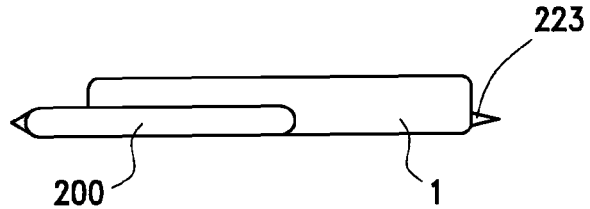

FIG. 14A is a top view of a 14B is a side view of another preferred embodiment of the invention. This embodiment is similar to the one shown in FIGS. 13B and 13C. However, the longer hook 200 is prolonged by a tip 203 that extends outwardly while the midsection of the hook extends parallel to the outer circumference of the ring structure. This configuration may help in the reexit of the hook from the lumen of the recipient vessel at 24 as shown in FIG. 8D.

FIG. 15A is a top view of a 15B is a side view of another preferred embodiment of the invention. This embodiment is similar to the one show in FIGS. 14A and 14B. However, both hooks (200, 220) have tips that extend upward out of the plane defined by the ring structure. This configuration may help in the reexit of both hooks at points 22 and 24 as shown in FIGS. 8B and 8D, respectively.

FIG. 16A is a top view of a 16B is a side view of another preferred embodiment of the invention. This embodiment is similar to the one show in FIGS. 15A and 15B. However, the tip 203 of the first hook 200 not only extends upwards, but also inwards towards the ring structure. This configuration may help in the entry of hook 200 at point 23 as shown in FIG. 8C into the lumen of the recipient vessel.

Figure 17A:
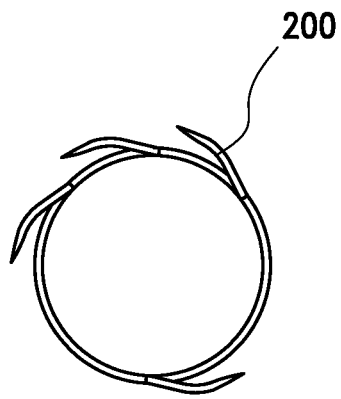
FIGS. 17A and 17B show an arrangement of four protruding pointed structures.
Figure 17B:
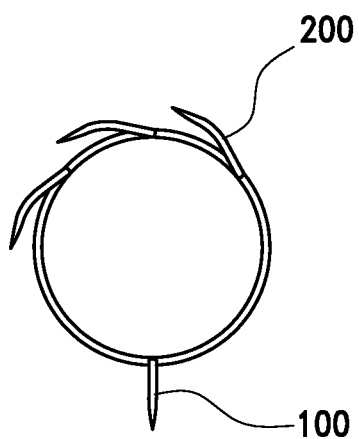

FIGS. 17A and 17B depict other multiple hookpin embodiments. FIG. 17A shows a four hook embodiment, with all hooks pointing into one direction. Three of the hooks 200 are clustered within one quarter of the ring at one end of the ring, with a single hook positioned at the opposing sides that fulfils the function of the pin in FIGS. 8A to 8E. FIG. 17B shows a variation of the embodiment shown in FIG. 17A, in which the single hook is a straight pin 100.

It will be appreciated that the methods and devices of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

The publications and other materials, including patents, used herein to illustrate the invention and the state of the art, and, in particular, to provide additional details respecting the practice of the invention are incorporated herein by reference in their entirety.

What is claimed is:

1. A method of connecting a donor vessel to a recipient vessel of a body comprising:
   employing a ring structure comprising a ring portion and at least two protruding pointed structures extending from the ring portion to attach said donor vessel to said recipient vessel wherein the donor vessel has a wall comprising an inner and an outer surface and an open end, with at least two incisions in the wall wherein the incisions are substantially evenly spaced around the circumference of the donor vessel, beginning at the open end of the donor vessel, and extending in an axial direction towards the ring structure and terminating at or before the ring structure to create at least two tail
   structures and an orifice reinforced by said ring structure;
   attaching the ring structure at said inner and/or outer surface of the donor vessel at a position proximate of said open end,
   establishing a contact between said donor vessel and said recipient vessel via said orifice; wherein said the recipient vessel, upon engagement with said ring structure via said protruding pointed structures, is stretched between about 10% and about 20% at least between at least two of said protruding pointed structures,
   forming a contact plane between the inner surface of said donor vessel at said tail structure and said wall of said recipient vessel; and
   attaching the donor vessel to the recipient vessel via said contact plane.

2. The method of claim 1, wherein a distance between said position of the ring structure and said orifice is about ½ to three times the diameter of said donor vessel.

3. The method of claim 1, wherein the incision terminates at a distance of between about ½ and about 2 times a thickness of the wall of said donor vessel.

4. The method of claim 1, wherein said ring structure is attached to the outer surface of said donor vessel.

5. The method of claim 1, wherein attaching the donor vessel to the recipient vessel via said contact plane essentially consists of applying an adhesive to at least parts of said contact plane.

6. The method of claim 5, wherein the recipient vessel is a blood vessel and the blood flow through said blood vessel is unoccluded at least up to forming a contact plane between the inner surface of said donor vessel at said tail structure and said wall of said recipient vessel 7. The method of claim 1, wherein said protruding pointed structures are attached symmetrically at said ring structure.

8. The method of claim 1, wherein at least a portion of a first of said protruding pointed structures extends substantially parallel to an outer circumference of the ring structure.

9. The method of claim 8 wherein at least a portion of a second of said protruding pointed structures extends straight from said ring structure and/or bends into a direction defined by said first protruding pointed structures.

10. The method of claim 9, wherein at
    least a portion of said second of said protruding pointed structures extends substantially
    parallel to the outer circumference of the ring structure.

11. The method of claim 10, wherein a
    proximal portion of at least one of said protruding pointed structures extends at an angle
    out of the plane defined by the ring structure.

12. The method of claim 11, wherein said
    angle is between about 10° and about 30°.

13. The method of claim 1, further comprising inserting a device into said donor vessel, wherein said device removes a portion of the wall of the recipient vessel to connect an interior of the donor vessel to an interior of the recipient vessel.

14. The method of claim 13, wherein said device is a laser catheter.

15. The method of claim 1, wherein the
    incision terminates at a distance of between about ½ and about 2 times the thickness of the wall of the donor vessel.

16. The method of claim 1, wherein the ring structure is attached to the outer surface of the donor vessel.

17. The method of claim 1, wherein the donor vessel comprises an even number of incisions.

18. A method of connecting a donor vessel to a recipient vessel of a body comprising:
    employing a ring structure comprising a ring portion and at least two protruding pointed structures extending from the ring portion to attach said donor vessel to said recipient vessel wherein the donor vessel has a wall comprising an inner and an outer surface and an open end, with at least two incisions in the wall wherein the incisions are substantially evenly spaced around the circumference of the donor vessel, beginning at the open end of the donor vessel, and extending in an axial direction towards the ring structure and terminating at or before the ring structure to create at least two tail
    structures and an orifice reinforced by said ring structure; attaching the ring structure at said inner and/or outer surface of the donor vessel at a position proximate of said open end,
    establishing a contact between said donor vessel and said recipient vessel via said orifice; wherein said the recipient vessel, upon engagement with said ring structure via said protruding pointed structures, is stretched between about 5% and about 30% at least between at least two of said protruding pointed structures.

forming a contact plane between the inner surface of said donor vessel at said tail structure and said wall of said recipient vessel; and attaching the donor vessel to the recipient vessel via said contact plane.

* * * * *

UNITED STATES PATENT AND TRADEMARK OFFICE
CERTIFICATE OF CORRECTION

PATENT NO. : 8,777,971 B2
APPLICATION NO. : 11/868446
DATED : July 15, 2014
INVENTOR(S) : Tulleken et al.

It is certified that error appears in the above-identified patent and that said Letters Patent is hereby corrected as shown below:

In the Claims

In column 17, line 46, in Claim 1, after "tail", delete "¶", therefor

In column 17, line 52, in Claim 1, after "said", delete "the", therefor

In column 18, line 11, in Claim 6, after "vessel", insert --.--, therefor

In column 18, line 57, in Claim 18, after "tail", delete "¶", therefor

In column 18, line 63, in Claim 18, after "said", delete "the", therefor

In column 18, line 67, in Claim 18, delete "structures." and insert --structures, and--, therefor Signed and Sealed this
Twenty-fifth Day of November, 2014

Michelle K. Lee
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,777,971 B2 | Page 1 of 1 |
| APPLICATION NO. | : 11/868446 | |
| DATED | : July 15, 2014 | |
| INVENTOR(S) | : Tulleken et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1589 days.

Signed and Sealed this
Nineteenth Day of January, 2016

Michelle K. Lee
*Director of the United States Patent and Trademark Office*